(12) United States Patent
McAteer et al.

(10) Patent No.: US 11,752,495 B2
(45) Date of Patent: Sep. 12, 2023

(54) ZEOLITE CATALYST

(71) Applicant: VERTELLUS HOLDINGS LLC, Indianapolis, IN (US)

(72) Inventors: Colin H. McAteer, Indianapolis, IN (US); Mirza S. Baig, Indianapolis, IN (US); Kayla L. Powell, Indianapolis, IN (US); James W. Shogren-Harris, St. Paul, MN (US); Rajamani Gounder, West Lafayette, IN (US)

(73) Assignee: VERTELLUS HOLDINGS LLC, Indianapolis, IN (US)

( * ) Notice: Subject to any disclaimer, the term of this patent is extended or adjusted under 35 U.S.C. 154(b) by 180 days.

(21) Appl. No.: 16/760,759

(22) PCT Filed: Nov. 1, 2018

(86) PCT No.: PCT/US2018/058703
§ 371 (c)(1),
(2) Date: Apr. 30, 2020

(87) PCT Pub. No.: WO2019/089920
PCT Pub. Date: May 9, 2019

(65) Prior Publication Data
US 2020/0338538 A1    Oct. 29, 2020

Related U.S. Application Data

(60) Provisional application No. 62/580,514, filed on Nov. 2, 2017.

(51) Int. Cl.
| | | |
|---|---|---|
| *C07D 213/10* | (2006.01) | |
| *B01J 29/70* | (2006.01) | |
| *B01J 37/00* | (2006.01) | |
| *B01J 37/03* | (2006.01) | |
| *B01J 37/04* | (2006.01) | |
| *C01B 39/06* | (2006.01) | |
| *C01B 39/46* | (2006.01) | |
| *C01B 39/08* | (2006.01) | |
| *B01J 35/00* | (2006.01) | |
| *B01J 29/90* | (2006.01) | |
| *B01J 29/76* | (2006.01) | |
| *B01J 37/02* | (2006.01) | |
| *B01J 38/02* | (2006.01) | |
| *C07D 213/09* | (2006.01) | |
| *C07D 213/02* | (2006.01) | |
| *C07D 213/04* | (2006.01) | |
| *C07D 213/08* | (2006.01) | |
| *C07D 213/00* | (2006.01) | |
| *C07D 213/06* | (2006.01) | |

(52) U.S. Cl.
CPC ....... *B01J 29/7057* (2013.01); *B01J 29/7615* (2013.01); *B01J 29/90* (2013.01); *B01J 35/002* (2013.01); *B01J 37/0018* (2013.01); *B01J 37/0209* (2013.01); *B01J 37/035* (2013.01); *B01J 37/036* (2013.01); *B01J 37/04* (2013.01); *B01J 38/02* (2013.01); *C01B 39/06* (2013.01); *C01B 39/08* (2013.01); *C01B 39/46* (2013.01); *C07D 213/00* (2013.01); *C07D 213/02* (2013.01); *C07D 213/04* (2013.01); *C07D 213/06* (2013.01); *C07D 213/08* (2013.01); *C07D 213/09* (2013.01); *C07D 213/10* (2013.01); *B01J 2229/16* (2013.01); *B01J 2229/37* (2013.01); *Y02P 20/584* (2015.11)

(58) Field of Classification Search
CPC .... B01J 29/90; B01J 2229/16; B01J 2229/18; B01J 2229/37; B01J 29/7057; B01J 29/7615; B01J 38/02; B01J 35/002; B01J 37/04; B01J 37/035; B01J 37/036; B01J 37/0209; B01J 37/0018; C01B 39/06; C01B 39/46; C01B 39/08; C07D 213/10; C07D 213/00; C07D 213/02; C07D 213/04; C07D 213/06; C07D 213/08; C07D 213/09; Y02P 20/584
USPC .......................................... 546/250, 251, 289
See application file for complete search history.

(56) References Cited

U.S. PATENT DOCUMENTS

| | | | |
|---|---|---|---|
| 4,960,894 A | 10/1990 | Hoelderich et al. | |
| 5,218,122 A * | 6/1993 | Goe ..................... | C07D 213/08 546/253 |
| 5,237,068 A | 8/1993 | Shimizu et al. | |
| 5,780,635 A * | 7/1998 | McAteer ............. | C07D 213/10 546/250 |
| 5,969,143 A * | 10/1999 | Chester ................ | C07D 213/08 546/250 |
| 5,994,550 A * | 11/1999 | Chitnis ................ | C07D 213/08 546/251 |
| 9,108,190 B1 * | 8/2015 | Fan ........................ | B01J 29/035 |
| 2010/0254894 A1 | 10/2010 | Wang et al. | |
| 2018/0057364 A1 * | 3/2018 | Gounder ................ | B01J 29/072 |

FOREIGN PATENT DOCUMENTS

WO    2015067654 A1    5/2015

OTHER PUBLICATIONS

PCT International Search Report and Written Opinion for PCT/US2018/058703, dated Jan. 22, 2019, 8 pages.
Chang C.-C, et al., "Rapid synthesis of Sn-Beta for the isomerization of cellulosic sugars", RSC Advances, 2012 vol. 2, issue 28, pp. 10475-10477.

(Continued)

*Primary Examiner* — Elizabeth D Wood
(74) *Attorney, Agent, or Firm* — Barnes & Thornburg LLP (57) ABSTRACT

The present disclosure relates to the preparation of pyridine derivatives, such as α-picoline or α-parvoline, and catalysts useful for the selective preparation of such pyridine derivatives. Particularly, the present disclosure relates to the selective preparation of certain pyridine derivative using dealuminated zeolite catalysts.

20 Claims, 1 Drawing Sheet

(56) References Cited

OTHER PUBLICATIONS

J. Dijkmans et al. Productive Sugar Isomerization with Highly Active Sn in Dealuminated β Zeolites, Green Chemistry, 2013, 15, 2777-2785.
J. Dijkmans et al. Cooperative Catalysis fir Multistep Biomass Conversion with Sn/Al Beta Zeolite, ACS Catalysis, 2015, 5, 928-940.
B. Tang et al. Improved Postsynthesis Strategy to Sn-Beta Zeolites as Lewis Acid Catalysts for the Ring-Opening lydration of Epoxides, ACS Catalysis, 2014, 4, 2801-2810.
C.C. Chang et al. Fluoride-free Synthesis of a Sn-BEA Catalysts by Dry Gel Conversion, Green Chemistry, 2015, 17, 2943-2951.
W.N.P. van der Graaf et al. Synthesis of Sn-Beta with Exclusive High Framework Sn Content, ChemCatChem, 2015, 7. 1152-1160.
P. Wolf et al. Post-synthetic Preparation of Sn-, Ti-, Zr-Beta: a Facile Route to Water Tolerant, Highly Active Lewis Acidic Zeolites, Dalton Trans., 2014, 43, 4514-4519.
C. Hammond et al. Simple and Scalable Preparation of Highly Active Lewis Acidic Sn-β, Angew. Chem. Int. Ed., 2012, 51, 11736-11739.
Extended European Search Report, prepared for EP Application No. 18872364, dated Mar. 11, 2021.

\* cited by examiner

ZEOLITE CATALYST

CROSS-REFERENCE TO RELATED APPLICATIONS

The present application is a national stage entry made under 35 U.S.C. § 371 of PCT International Application No. PCT/US2018/058703, filed Nov. 1, 2018, which claims under 35 U.S.C. § 119(e) the benefit of and priority to U.S. Patent Application No. 62/580,514, filed Nov. 2, 2017, the disclosures of which are incorporated herein by reference in their entirety.

TECHNICAL FIELD

The present disclosure relates to the preparation of pyridine derivatives, such as α-picoline or α-parvoline, and catalysts useful for the selective preparation of such pyridine derivatives. Particularly, the present disclosure relates to the selective preparation of certain pyridine derivatives using dealuminated zeolite catalysts.

BACKGROUND

The present disclosure relates to a process for the preparation of pyridine base synthesis using modified zeolite catalysts.

Pyridine bases are the largest volume of heteroaromatic compounds to be prepared industrially by the use of heterogeneous catalysts. Within this group, pyridine and picolines (methylpyridines) are dominant over lutidines (dimethylpyridines), collidines (trimethylpyridines and methylethylpyridines), and parvolines (dimethylethylpyridines). Pyridine bases are key precursors to a range of agrochemical, pharmaceutical, and consumer products and are used directly in solvent and acid-scavenger applications.

The term "base synthesis" is known and used in the pyridine field and in this application to identify a process by which bases of pyridine or alkylpyridine derivatives are prepared by reacting aldehydes and/or ketones with ammonia in the gas phase using a heterogeneous catalyst. Some examples of base synthesis reactions (and their common names where appropriate) include, for example, the synthesis of α- and γ-picoline from acetaldehyde and ammonia (the "alpha-gamma reaction"); the synthesis of α-parvoline (2-ethyl-3,5-dimethylpyridine) from propionaldehyde and ammonia; the synthesis of 2-propyl-3,5-diethylpyridine; and the like. Many other base synthesis reactions are known and reported, or practiced in the art, but those reactions involving the reaction of an aldehyde with ammonia are those that are of particular interest in the present disclosure. Furthermore, much of the industrial scale synthesis of pyridine bases takes place in the vapor phase using ammonia in combination with carbonyl compounds (aldehydes and ketones) in contact with a heterogeneous catalyst. Coproduct isomers α- and γ-picoline can be produced from acetaldehyde-ammonia feed mixtures ("alpha-gamma reaction").

Catalysts known in the art for carrying out the base synthesis reactions of interest in the present disclosure include alumina, either alone or as a support for zinc fluoride or other metal salts, or as an amorphous structure incorporating both silica and alumina (See U.S. Pat. Nos. 2,807,618 and 2,744,904; and German Patent No. 1,255,661), and shape-selective zeolites which are aluminosilicates of definite crystal structure having activities and pores of a size similar to that of other commercially-interesting molecules (See, e.g., E. G. Derouane, "New Aspects of Molecular Shape-Selectivity: Catalysis by Zeolite ZSM-5", Catalysis by Zeolites, ed. B. Imelik et al., Elsevier, Amsterdam, pp. 5-18 (1980)).

Zeolites are defined as microporous (≤20 Å channel apertures) crystalline aluminosilicates and include both naturally occurring minerals and man-made synthetic materials. Zeolites are long known to be useful as selective adsorbents and catalysts due to their channel size(s) being comparable in size to many molecules. Microporous zeolites may be subdivided into small (≤5 Å), medium (5-6 Å), and large (≥6 Å) pore channels for those containing ≤8, 10, and ≥12 T-atom rings, respectively. (T-atom refers to tetrahedral atoms that are either Si or Al each surrounded by 4 oxygen atoms.) Zeolites are known having channel structures of different dimensionalities (i.e., 1-, 2-, and 3-D) often with interconnecting channels of different sizes and occasionally with separate channel systems that are not interconnected.

Formally, a pure all-silica zeolite has a framework that is charge neutral. Isomorphous substitution of a $Si^{IV}$ atom by $Al^{III}$ introduces a negative charge on the zeolite framework that is compensated by having a cationic species residing in close proximity within the zeolite channel. Ion exchange procedures allow the cationic species to be changed as desired (e.g., from $Na^+$ in an as-synthesized zeolite to a proton—i.e., $H^+$-essentially providing a solid acid catalyst). A wide range of cations, including metal, organic, and organometallic species, can be introduced into a zeolite's channels. The overall amount of such species will depend on the zeolite and its molar $SiO_2/Al_2O_3$ ratio.

Zeolite Beta (BEA), originally discovered by Mobil Oil corp. in 1967 (U.S. Pat. No. 3,308,069), has a 3-D channel structure featuring linear channels (ca. 7.6×6.4 Å) in two dimensions and a tortuous channel (5.5×5.5 Å) in the third dimension. Zeolite Beta became commercially available in the early 1990s typically supplied in its ammonium ion ($NH_4^+$-BEA) and proton ($H^+$-BEA) forms with as-synthesized $SiO_2/Al_2O_3$ molar ratios of ca. 25-75. Zeolite Beta has been used in the synthesis of pyridine bases, primarily the synthesis of pyridine and beta-picoline from acetaldehyde and formaldehyde (the so-called "pyridine-beta reaction"), where the zeolite beta has a $SiO_2/Al_2O_3$ of about 15 to 90 (equivalent to Si/Al=7.5 to 45) and metal ion, such as Pb, Co, Sn, Cd, Ga, Tl incorporated therein (See U.S. Pat. No. 5,780,635).

Reactor designs for these heterogeneous gas-phase reactions have varied within the basic categories of fixed-bed and fluid-bed forms. The advantages of fluidized beds were recognized early-on (see U.S. Pat. No. 2,807,618) as evidenced by the fact that the early commercial-scale base synthesis units used fluidized beds, and that most units brought into operation since then incorporate fluidized catalyst beds. One reason for this is that base synthesis reactions always produce deposits of dark, mostly carbonaceous materials referred to as "coke" which tend to foul the catalyst thereby gradually reducing its activity. Although variations are observed, all catalysts accumulate these coke deposits at an appreciable rate such that periodic action is required. As discarding catalyst is not desirable for economic reasons, regeneration by heating in air or other oxygen-containing gases is commonly employed. This regeneration/combustion process is very exothermic and also best carried out in a fluid bed process. C. L. Thomas, "Catalytic Processes and Proven Catalysts", Academic Press, New York, pp. 11-14 (1970).

Accordingly, a common technique has long been to run two fluid beds concurrently, one for reaction and one for regeneration, with catalyst continuously or intermittently cycled between the beds. Operating parameters such as circulation rates, contact times, temperatures and the like are readily determined by skilled operators in view of the specific reactions and/or ingredients used. See, e.g., German Patent No. 2,203,384. An ancillary benefit of this technique is that product yields from base synthesis reactions carried out in fluidized beds are recognized to be generally higher than in corresponding fixed-bed reactions (See, BP Chemicals U.K. Ltd. of London, England), one for alpha-gamma synthesis (British Patent No. 1,188,891; German Patent 1,903,879; and Canadian Patent No. 852,745) and the other for. pyridine-beta synthesis (British Patent No. 1,235,390 Canadian Patent No. 851,727; and German Patent No. 1,903,878).

Similar advantages of fluid-bed usage were reported by Feitler et al. in U.S. Pat. No. 4,675,410 for base synthesis catalysts composed of shape-selective aluminosilicates (commonly referred to as "zeolites") used in their acidic form. These crystalline zeolites had earlier been reported for base synthesis reactions by Chang et al. in U.S. Pat. No. 4,220,783 both in their acid- or H-form and as ion-exchanged with cadmium, copper or nickel. Several examples in the Chang patent demonstrated deactivation of the catalyst over time thereby also suggesting the desirability of a fluid-bed to reactivate the catalyst by heating in air in any commercial application.

However, because catalyst will inevitably escape from fluid-bed reactors and pyridine base syntheses generate a large amount of waste water, one constraint on the commercial viability of pyridine base reactions is the use of toxic metal promoters such as lead, thallium, and cadmium can result in toxic waste-water output.

Because the marketplace requirement for α-picoline and its derivatives considerably exceed those of γ-picoline and its derivatives, there exists a strong need for the development of new catalysts that provide high selectivity and yield of pyridine bases, such as α-picoline. Furthermore, market pressures demand the development of new catalysts that provide high selectivity ratios of desired pyridine bases, such as α-picoline and pyridine versus undesired pyridine bases such as γ-picoline and higher alkylated pyridine bases, and versus by-products such as acetonitrile. It is a further aim of the present disclosure to provide new catalysts that incorporate non-toxic metals into the catalyst formulation.

SUMMARY

In one aspect the present disclosure relates to a process for preparing a pyridine base comprising contacting ammonia with a $C_2$-$C_6$ aldehyde in the presence of a metal loaded zeolite beta catalyst comprising a metal and a zeolite beta.

In another aspect, the present disclosure relates to a process for preparing a pyridine base comprising contacting ammonia with a $C_2$-$C_6$ aldehyde in the presence of a metal loaded zeolite beta catalyst comprising a metal and a zeolite beta, wherein the metal loaded zeolite beta catalyst is prepared by a process comprising
  i. contacting tetraethyl orthosilicate with aqueous tertaethylammonium hydroxide to provide a silicate solution;
  ii. contacting the silicate solution with a metal source to provide a metal-silicate solution;
  iii. contacting the metal-silicate solution with hydrofluoric acid to provide a metal-silicate gel; and
  iv. contacting the metal-silicate gel with dealuminated zeolite beta seeds to provide the metal loaded zeolite beta catalyst.

In some embodiments in connection with this aspect, the metal loaded zeolite beta catalyst is substantially free of $Al_2O_3$. In some embodiments in connection with this aspect, the metal loaded zeolite beta catalyst has a $SiO_2/Al_2O_3$ molar ratio of at least about 200/1. In some embodiments, the metal loaded zeolite beta catalyst has a $SiO_2/Al_2O_3$ molar ratio of at least about 400/1. In some embodiments in connection with this aspect, the metal loaded zeolite beta catalyst has a $SiO_2/Al_2O_3$ molar ratio of at least about 500/1.

In another aspect, the present disclosure relates to a process for preparing a pyridine base comprising contacting ammonia with a $C_2$-$C_6$ aldehyde in the presence of a metal loaded zeolite beta catalyst comprising a metal and a zeolite beta, wherein the metal loaded zeolite beta catalyst comprises a metal and a dealuminated zeolite beta. In some embodiments in connection with this aspect, the dealuminated zeolite beta has a $SiO_2/Al_2O_3$ molar ratio of at least about 150/1. In some embodiments in connection with this aspect, the dealuminated zeolite beta has a $SiO_2/Al_2O_3$ molar ratio of at least about 200/1.

In some embodiments in connection with this aspect, the metal loaded zeolite beta catalyst is prepared by a process comprising
  i. contacting a dealuminated zeolite beta with a metal source to provide the metal loaded zeolite beta catalyst.

In some embodiments in connection with this aspect, the dealuminated zeolite beta is prepared by a process comprising
  ii. contacting a zeolite beta catalyst having a $SiO_2/Al_2O_3$ molar ratio of about 15 to about 90 with a mineral acid to provide the dealuminated zeolite beta.

The process of the present disclosure can be described as embodiments in any of the following enumerated clauses. It will be understood that any of the embodiments described herein can be used in connection with any other embodiments described herein to the extent that the embodiments do not contradict one another.

1. A process for preparing a pyridine base comprising
  a. contacting ammonia with a $C_2$-$C_6$ aldehyde in the presence of a metal loaded zeolite beta catalyst comprising a metal and a zeolite beta.
2. The process of clause 1, wherein the metal loaded zeolite beta catalyst is prepared by a process comprising
  i. contacting tetraethyl orthosilicate with aqueous tertaethylammonium hydroxide to provide a silicate solution;
  ii. contacting the silicate solution with a metal source to provide a metal-silicate solution;
  iii. contacting the metal-silicate solution with hydrofluoric acid to provide a metal-silicate gel; and
  iv. contacting the metal-silicate gel with dealuminated zeolite beta seeds to provide the metal loaded zeolite beta catalyst.
3. The process of clause 1 or 2, wherein the metal source is a Sn containing compound.
4. The process of clause 1 or 2, wherein the metal source is aqueous stannic chloride.
5. The process of any one of the preceding clauses, wherein the metal loaded zeolite beta catalyst has a zeolite beta topology and the absence of bulk crystalline $SnO_2$.
6. The process of any one of the preceding clauses, wherein the tin content of the metal loaded zeolite beta catalyst is from about 1 wt % to about 4 wt %.
7. The process of any one of the preceding clauses, wherein the metal loaded zeolite beta catalyst comprises a metal and a dealuminated zeolite beta.
8. The process of any one of the preceding clauses, wherein the dealuminated zeolite beta has a $SiO_2/Al_2O_3$ molar ratio of at least about 150/1.

9. The process of any one of the preceding clauses, wherein the dealuminated zeolite beta has a $SiO_2/Al_2O_3$ molar ratio of at least about 200/1.

10. The process of any one of the preceding clauses, wherein the metal is in an amount of less than about 10% by weight, or less than about 5% by weight, or less than about 4% by weight, or less than about 3% by weight compared to the metal loaded zeolite beta catalyst.

11. The process of any one of the preceding clauses, wherein the metal selected from the group consisting of Sn, Ti, Mn, Fe, Co, Zn, and combinations thereof.

12. The process of any one of the preceding clauses, wherein the metal comprises Sn.

13. The process of clause 12, wherein the metal further comprising Mn or Zn.

14. The process of any one of the preceding clauses, wherein the metal is a combination of Sn and Mn in a ratio of about 3:1 to about 10:1.

15. The process of any one of the preceding clauses, wherein the metal is a combination of Sn and Zn in a ratio of about 3:1 to about 10:1.

16. The process of any one of the preceding clauses, wherein the metal comprises Zn.

17. The process of any one of the preceding clauses, wherein the metal comprises Ti.

18. The process of any one of the preceding clauses, wherein the metal comprises Mn.

19. The process of any one of the preceding clauses, wherein the metal loaded zeolite beta catalyst is prepared by a process comprising
   i. contacting a dealuminated zeolite beta with a metal source to provide the metal loaded zeolite beta catalyst.

20. The process of any one of the preceding clauses, wherein the metal source is $SnO_2$, $SnCl_4$, $SnSO_4$ or $Sn(CH_3CO_2)_2$.

21. The process of any one of the preceding clauses, wherein the metal source provides a metal oxide in the metal loaded zeolite beta catalyst.

22. The process of any one of the preceding clauses, wherein the metal oxide is $SnO_2$, $ZnO$, $Fe_2O_3$, $Co_3O_4$, $MnO_2$ or $TiO_2$.

23. The process of any one of the preceding clauses, further comprising
   ii. contacting a zeolite beta catalyst having a $SiO_2/Al_2O_3$ molar ratio of about 15 to about 90 with a mineral acid to provide the dealuminated zeolite beta.

24. The process of any one of the preceding clauses, wherein the mineral acid is selected from the group consisting of nitric acid, hydrochloric acid and phosphoric acid.

25. The process of any one of the preceding clauses, wherein the metal loaded zeolite beta catalyst is mixed and formed with a binder selected from the group consisting of $SiO_2$, $Al_2O_3$, kaolin, montmorillonite, and titania to provide a metal loaded zeolite beta catalyst composition.

26. The process of any one of the preceding clauses, wherein the metal loaded dealuminated zeolite catalyst composition is formed into an extrudate, a tablet, a sphere or a microsphere.

27. The process of any one of the preceding clauses, wherein the $C_2$-$C_6$ aldehyde is selected from the group consisting of acetaldehyde, propionaldehyde, crotonaldehyde and butyraldehyde.

28. The process of any one of the preceding clauses, wherein the $C_2$-$C_6$ aldehyde is acetaldehyde or propionaldehyde.

29. The process of any one of the preceding clauses, wherein contacting takes place at a temperature of from about 300° C. to about 500° C.

30. The process of any one of the preceding clauses further comprising
   b. regenerating the metal loaded zeolite beta catalyst remaining after step (a) by contacting the metal loaded zeolite beta catalyst with air at a temperature of from about 500° C. to about 600° C.

31. The process of any one of the preceding clauses, further comprising contacting ammonia with a $C_2$-$C_6$ aldehyde in the presence of the metal loaded zeolite beta catalyst obtained from step (b).

32. The process of any one of the preceding clauses, wherein step (a) is carried out at a temperature of about 380° C. to about 450° C.

33. The process of any one of the preceding clauses, wherein the pyridine base is α-picoline.

34. The process of any one of the preceding clauses, wherein the pyridine base is α-picoline and the α-picoline is formed in a ratio of at least about 2.5:1 of α-picoline to γ-picoline side-product.

35. The process of any one of the preceding clauses, wherein the pyridine base is α-picoline and the α-picoline is formed in a ratio of at least about 10:1 of α-picoline to pyridine side-product.

36. The process of any one of the preceding clauses, wherein the pyridine base is α-picoline and the α-picoline is formed in a ratio of at least about 5:1 of α-picoline to acetonitrile side-product.

37. The process of any one of clauses 1 to 32, wherein the pyridine base is α-parvoline.

DETAILED DESCRIPTION

For the purposes of promoting an understanding of the principles of the present disclosure, reference will now be made to certain embodiments thereof and specific language will be used to describe the same. It will nevertheless be understood that no limitation of the scope of the disclosure is thereby intended, such alterations and further modifications of these embodiments, and such further applications of the principles of the invention as described herein being contemplated as would normally occur to one skilled in the art to which the disclosure relates.

As described above, one preferred embodiment of the present invention relates to the discovery of a new base synthesis process for the preparation of pyridine bases involving the catalytic reaction of one or more aldehydes containing from two to about six carbon atoms with ammonia in the gas phase. The reaction is carried out in the presence of an effective amount of a metal loaded zeolite beta catalyst comprising a metal and a zeolite beta. Metal loaded zeolite beta catalysts can be prepared by several means, including the hydrothermal synthesis of zeolite beta followed by the impregnation of a metal onto the newly formed catalyst via a metal source. Alternatively, a commercially available zeolite beta having a $SiO_2/Al_2O_3$ molar ratio of about 15 to about 90 can be dealuminated, followed by the introduction of a metal into the catalyst structure via a metal source.

In some embodiments, an exemplary hydrothermal preparation method found at Chang et al., *RSC Advances* 2012, 2, 10475-10477 can be used in connection with the processes described herein. The method described in Chang et al. was carried out in connection with the present disclosure as Example 1. The characteristics of the metal loaded zeolite beta catalyst prepared according to the Chang et al. procedure were consistent with the reported literature, and the benefits and uses as described herein. It will be appreciated that modifications to the method and reagents used in connection with the Chang et al. procedure and Example 1 provided below are contemplated by the disclosure, and can be implemented by one of skill in the art to the extent that such changes are consistent with the catalyst characteristics, and the benefits and uses as described herein. Furthermore, one of skill in the art will appreciate that other hydrothermal methods for preparing zeolite beta catalysts can also be applied to the present disclosure. Alternatively, zeolite beta with framework Zn atoms (CIT-6) can be prepared using the procedure reported by Davis et al., (*J. Phys. Chem. B.* 1999, 103, 2674-2679).

Alternatively, the processes described herein can be carried out with a metal loaded zeolite beta catalyst derived from commercially available zeolite beta, such as $NH_4$—BEA(25), (available from Zeolyst), $NH_4$—BEA(38), (available from, for example Zeolyst or Alfa Aesar), and the like. In some embodiments, the starting zeolite beta can have a $SiO_2/Al_2O_3$ molar ratio of about 15 to about 90. The starting zeolite beta can be dealuminated by treatment of the zeolite beta with a mineral acid, such as nitric acid. An exemplary nitric acid dealumination procedure found at Sels et al. (*Green Chemistry* 2013, 15, 2777-2785) can be used in connection with the processes described herein. The method described in Sels et al. was carried out in connection with the present disclosure in the Examples provided below. The characteristics of the metal loaded zeolite beta catalyst prepared according to the Sels et al. procedure were consistent with the reported literature, and the benefits and uses as described herein.

Once the dealuminated zeolite beta (also referred to as deAlBEA) is prepared, a metal can be introduced to the composition to provide a metal loaded zeolite beta catalyst as described herein. The metal can be introduced by a metal source as described herein, and can be introduced by a variety of methods known in the art. For example, the dealuminated zeolite beta can be subjected to a metal grafting procedure, such as contacting the dealuminated zeolite beta with a metal source, such as $SnCl_4.5H_2O$, in the presence of a solvent, such as an alcohol solvent, such as isopropanol, at reflux. Alternatively, the dealuminated zeolite beta can be subjected to an incipient wetness impregnation (IWI) procedure, such as contacting the dealuminated zeolite beta with an aqueous metal source, such as aqueous $SnSO_4$, to incorporate the metal into the catalyst. Exemplary methods of metal grafting and IWI are provided in the examples described herein. It will be appreciated that modifications to the method and reagents used in connection with the examples provided below for metal grafting and IWI procedures are contemplated by the disclosure, and can be implemented by one of skill in the art to the extent that such changes are consistent with the catalyst characteristics, and the benefits and uses as described herein.

The identity of the metal useful in connection with the processes described herein can be a variety of metals, such as Sn, Ti, Mn, Fe, Zn, and the like, and combinations thereof. In some embodiments, the metal is Sn. In some embodiments, the metal source for introducing metal into catalysts described herein can be any metal salt of metal compound known in the art in connection with catalysts preparations, including but not limited to, stannic chloride pentahydrate, aqueous stannous sulfate, stannous acetate, such as a solution in i-PrOH, zinc acetate dehydrate, tin(II) acetate, an aqueous solution of Mn(II), Fe(III), Co(II), and Zn(II) nitrate salts, and the like. It will be appreciated that after introduction of the metal source in catalysts as described herein, the metal can be in the form of a metal oxide, such as $SnO_2$, $ZnO$, $Fe_2O_3$, $Co_3O_4$, $MnO_2$, or $TiO_2$, and the like.

It will be appreciated that the metal loading on zeolite beta catalysts useful in connection with processes as described herein can be varied depending on reaction conditions, reactant identity, and the like. In some embodiments, the metal is in an amount of less than about 10% by weight, or less than about 5% by weight, or less than about 4% by weight, or less than about 3% by weight compared to the metal loaded zeolite beta catalyst. In some embodiments, the nominal loading of $M_yO_x$ can be between about 0.4 wt % to about 5.0 wt % based of the zeolite beta. In some embodiments, the nominal loading of $M_yO_x$ can be between about 1.0 wt % to about 5.0 wt % based of the zeolite beta. In some embodiments, the nominal loading of $M_yO_x$ can be between about 2.0 wt % to about 4.0 wt % based of the zeolite beta. It will be appreciated that the nominal loading of $M_yO_x$ on the zeolite beta catalyst can be any range of any value between about 0.4 wt % and about 5 wt %, such as 0.4 wt %, 0.5 wt %, 0.6 wt %, 0.7 wt %, 0.8 wt %, 0.9 wt %, 1.0 wt %, 1.2 wt %, 1.4 wt %, 1.6 wt %, 1.8 wt %, 2.0 wt %, 2.4 wt %, 2.6 wt %, 3.0 wt %, 3.5 wt %, 4.0 wt %, 4.2 wt %, 4.4 wt %, 4.5 wt %, 4.6 wt %, 4.8 wt %, and 5.0 wt %.

In some embodiments of the processes described herein, zeolite beta useful for preparing catalysts described herein has a silica to alumina ratio of about 100 or more. In some embodiments, the zeolite beta has a silica to alumina ratio of about 200 or more. In some embodiments, the zeolite beta has a silica to alumina ratio of about 300 or more. In some embodiments, the zeolite beta is substantially free of alumina. It will be appreciated that all values of silica/alumina ratio included within the ranges provided are described.

It will be appreciated that catalysts useful in connection with the present teachings may also include a binder useful, for example for holding the components of a catalyst composition together. It is also within the scope of the description that the binder can also provide some catalytic activity. Suitable binders contemplated for use in the catalyst compositions of the invention typically include, but are not limited, to silica, alumina, silica-alumina and combinations thereof. In a some embodiments, the binder is silica. In some embodiments, the silica binder is derived from colloidal silica, silicates, silicic acid, tetraalkoxysilanes and/or other silicon precursor compounds.

Catalysts useful in connection with the present teachings may also include clay. Examples of suitable clay components include, but are not limited to kaolin, modified kaolin (e.g. metakaolin), montmorillonite, pillared clay, and the like. It will be appreciated that the identity of the clay additive is not particularly limited, and that virtually any clay known in the art for use in connection with zeolite catalysts can be used.

The metal loaded zeolite beta catalyst compositions used in connection with the present teachings are useful in a pyridine base synthesis process typically operated in a fixed bed or fluidized bed reactor, to achieve an overall increase in pyridine base yields. The catalyst compositions can be shaped and formed as extrudates, tablets or spheres with dimensions ranging from 0.5 to 10 mm in size suitable for use in a fixed bed reactor. Further the catalyst compositions in the form of microspheres having a particle size and an attrition property sufficient to affect fluidization properties within a fluidized bed reactor. When used in a fluidized bed reactor, metal loaded zeolite beta catalyst compositions useful in connection with the present teachings can have a mean particle size of about 40 m to about 200 m. In some embodiments, metal loaded zeolite beta catalyst compositions have a mean particles size ranging from about 60 m to about 120 m.

Many base synthesis processes are known and are also contemplated to be within the scope of the processes described herein. In addition to the specific Examples below and to the descriptions mentioned above, the alpha-gamma reaction is generally carried out with a feed molar ratio of ammonia to acetaldehyde of about 1:1. In some embodiments, the feed ratio can be about 3:1 to about 0.4:1. The individual flows of acetaldehyde and ammonia combine in the presence of a fixed bed catalyst for a duration that is often defined as the contact time that in turn depends upon the catalyst bed volume, reactor dimensions, reaction temperature, and feed flow rates for a given feed composition. For convenience, the W/F factor is the preferred measure for both fixed and fluidized catalyst beds and is defined as the weight amount of catalyst used (W) divided by the hourly weight of acetaldehyde fed (F) whose units can be expressed as grams of catalyst per gram of acetaldehyde per hour (g-cat/g-CH$_3$CHO/h). In some embodiments, the W/F useful in connection with the present teachings can be from about 0.2 to about 5. In some embodiments, the W/F useful in connection with the present teachings can be at least about 0.3. In some embodiments, the W/F useful in connection with the present teachings can be about 0.6. In some embodiments, the contact time useful in connection with the present teachings can be from about 0.2 to about 10 seconds. In some embodiments, the contact time useful in connection with the present teachings can be at least about 1 second. In some embodiments, the contact time useful in connection with the present teachings can be about 2 seconds.

It will be appreciated that the above feed ratios and feed rates can be applied to and modified for other C$_2$-C$_6$ aldehydes useful in connection with the processes described herein to prepare other pyridine bases. For example, replacing acetaldehyde with propanaldehyde for the preparation of α-parvoline can be carried out according to the ratios and rates described above.

It will be appreciated that additional solvents may be used in connection with the processes of the present as are conventionally known in the art for pyridine base synthesis processes. The temperature of the reaction of the present disclosure can be between about 300° C. and about 500 CC. The temperature of the reaction of the present disclosure can be between about 350° C. and about 550° C. In some embodiments, the temperature can be between about 380° C. and about 450° C. In some embodiments, the temperature can be between about 380° C. In some embodiments, the temperature can be between about 390° C. In some embodiments, the temperature can be between about 400° C. In some embodiments, the temperature can be between about 410° C. In some embodiments, the temperature can be between about 420° C. In some embodiments, the temperature can be between about 430° C. In some embodiments, the temperature is about 440° C. In some embodiments, the temperature is about 450° C.

The products of some processes described herein, being α-picoline, γ-picoline, pyridine, and CH$_3$CN, can be condensed and separated into pure compounds by drying and distillation as is well known in the art. In some embodiments, the processes described herein can produce α-picoline and γ-picoline in a ratio of at least about 2.5:1 of α-picoline to γ-picoline side-product. In some embodiments, the processes described herein can produce α-picoline and γ-picoline in a ratio of at least about 2.6:1 of α-picoline to γ-picoline side-product. In some embodiments, the processes described herein can produce α-picoline and γ-picoline in a ratio of at least about 3.0:1 of α-picoline to γ-picoline side-product. In some embodiments, the processes described herein can produce α-picoline and γ-picoline in a ratio of at least about 3.5:1 of α-picoline to γ-picoline side-product. In some embodiments, the processes described herein can produce α-picoline and γ-picoline in a ratio of at least about 3.6:1 of α-picoline to γ-picoline side-product. In some embodiments, the processes described herein can produce α-picoline and γ-picoline in a ratio of at least about 4.0:1 of α-picoline to γ-picoline side-product.

In some embodiments, the processes described herein can produce α-picoline and γ-picoline in a ratio of at least about 10:1 of α-picoline to pyridine side-product. In some embodiments, the processes described herein can produce α-picoline and γ-picoline in a ratio of at least about 15:1 of α-picoline to pyridine side-product. In some embodiments, the processes described herein can produce α-picoline and -picoline in a ratio of at least about 20:1 of α-picoline to pyridine side-product. In some embodiments, the processes described herein can produce α-picoline and -picoline in a ratio of at least about 25:1 of α-picoline to pyridine side-product. In some embodiments, the processes described herein can produce α-picoline and γ-picoline in a ratio of at least about 30:1 of α-picoline to pyridine side-product. In some embodiments, the processes described herein can produce α-picoline and γ-picoline in a ratio of at least about 35:1 of α-picoline to pyridine side-product. In some embodiments, the processes described herein can produce α-picoline and -picoline in a ratio of at least about 40:1 of α-picoline to pyridine side-product. In some embodiments, the processes described herein can produce α-picoline and -picoline in a ratio of at least about 45:1 of α-picoline to pyridine side-product. In some embodiments, the processes described herein can produce α-picoline and γ-picoline in a ratio of at least about 50:1 of α-picoline to pyridine side-product.

In some embodiments, the processes described herein can produce α-picoline and γ-picoline in a ratio of at least about 4:1 of α-picoline acetonitrile side-product. In some embodiments, the processes described herein can produce α-picoline and γ-picoline in a ratio of at least about 5:1 of α-picoline acetonitrile side-product. In some embodiments, the processes described herein can produce α-picoline and -picoline in a ratio of at least about 6:1 of α-picoline acetonitrile side-product. In some embodiments, the processes described herein can produce α-picoline and -picoline in a ratio of at least about 7:1 of α-picoline acetonitrile side-product. In some embodiments, the processes described herein can produce α-picoline and γ-picoline in a ratio of at least about 8:1 of α-picoline acetonitrile side-product. In some embodiments, the processes described herein can produce α-picoline and γ-picoline in a ratio of at least about 10:1 of α-picoline acetonitrile side-product. In some embodiments, the processes described herein can produce α-picoline and -picoline in a ratio of at least about 15:1 of α-picoline acetonitrile side-product. In some embodiments, the processes described herein can produce α-picoline and -picoline in a ratio of at least about 20:1 of α-picoline acetonitrile side-product. In some embodiments, the processes described herein can produce α-picoline and γ-picoline in a ratio of at least about 25:1 of α-picoline acetonitrile side-product.

Likewise, products of some processes described herein, being α-parvoline and 7-parvoline, can be condensed and separated into pure compounds by drying and distillation as is well known in the art. In some embodiments, the processes described herein can produce α-parvoline and γ-parvoline in a ratio of at least about 50:1 of α-parvoline to γ-parvoline side-product. In some embodiments, the processes described herein can produce α-parvoline and γ-parvoline in a ratio of at least about 55:1 of α-parvoline to γ-parvoline side-product. In some embodiments, the processes described herein can produce α-parvoline and γ-parvoline in a ratio of at least about 60:1 of α-parvoline to γ-parvoline side-product.

To further illustrate the present disclosure and the advantages thereof, the following specific examples are given. The examples are given as illustrations of the disclosure. It should be understood, however, that the disclosure is not limited to the specific details set forth in the examples.

All parts and percentages in the examples as well as the remainder of the description that refers to solid compositions or concentrations are by weight unless otherwise specified. However, all parts and percentages in the examples as well as the remainder of the specification referring to gas compositions are molar or by volume unless otherwise specified.

Further, any range of numbers recited in the disclosure or claims, such as that representing a particular set of properties, units of measure, conditions, physical states or percentages, is intended to literally incorporate expressly herein by reference or otherwise, any number falling within such range, including any subset of numbers within any range so recited.

The yields of products described herein, it will be appreciated that the "weight yield" of a product is used as commonly known in the art. Specifically, the weight yield can be defined according to the general equation:

Compound weight yield=Weight yield of compound produced/Weight of reactant aldehyde used In the case of three moles of acetaldehyde forming one mole of α-picoline, the maximum theoretical weight yield is 93.13 gα-picoline/3×44.05 g acetaldehyde=0.7047

The weight yield can be converted into molar yield using the equation:

% molar yield(Weight Yield/0.7047)×100

EXAMPLES

Example 1: Hydrothermal Synthesis of Sn-BEA

Sn-BEA was synthesized hydrothermally using a synthesis method reported by Chang et al., (*RSC Advances* 2012, 2, 10475-10477) in which micro-filtered, dealuminated BEA particles (<200 nm diameter) were used as the seed material.

Dealuminated BEA seeds were prepared by adding 0.92 g of $NH_4$—BEA(38) sample (Zeolyst, CP814C, $SiO_2$/$Al_2O_3$~38 or Si:Al ca. 19:1) to 23 mL of a 13M $HNO_3$ solution in a PTFE jar. This solution was stirred overnight at 80° C. and the solids were collected by centrifugation and washed thoroughly with deionized water (18.2 MΩ/cm) until a neutral pH was reached. The recovered solids were dried overnight at 100° C. The final molar Si:Al ratio was >660:1 as determined by atomic absorption spectroscopy (AAS, HF dissolution).

The starting gel for Sn-BEA was prepared by combining 20.59 g tetraethyl orthosilicate (TEOS, 98%, Sigma Aldrich) and 23.05 g aqueous tetraethylammonium hydroxide solution (TEAOH, Sachem, 35 wt. %) in a PTFE jar, and allowing these to homogenize for 1 h. Then, 0.30 g of stannic chloride pentahydrate ($SnCl_4$-$5H_2O$, 98%, Sigma Aldrich) was dissolved in 1.91 g water and this solution was added dropwise to the stirring gel, which was left stirring in a closed PTFE jar overnight (>12 h). Afterward, the ethanol generated from hydrolysis of TEOS and some excess $H_2O$ was evaporated from the gel while it was stirring, with a final weight loss of 23.84 g. Next, 2.2 g of aqueous hydrofluoric acid (Alfa Aesar, 48%) was added into the solution and stirred with a Teflon spatula. Then, 1.61 mL $H_2O$ and 0.25 g dealuminated BEA seeds were added to the gel (~4 wt. % of the $SiO_2$ content) and stirred with a Teflon spatula. The final gel molar composition was 0.56 TEAOH: 1 $SiO_2$: 0.0086 $SnCl_4$: 0.54 HF: 8.38 $H_2O$. This gel was loaded into a Teflon-lined stainless steel autoclave and heated at 140° C. under rotation (60 rpm) for 6 days. The resulting solids were recovered by centrifugation and washed thoroughly with water and acetone. The recovered solids were oven dried overnight (100° C.) and calcined in a muffle furnace under flowing air (65 mL/g solids, 1° C./min) at 580° C. for 10 h. The XRD of the Sn-BEA (FIG. 1) confirmed the presence of the BEA topology and the absence of bulk crystalline $SnO_2$ (Cassiterite). The tin content was determined to be 1.30 wt. % (equivalent to 1.65 wt. % $SnO_2$) by AAS.

The Sn-BEA powder was pressed (10 tons, 3 mm OD die) and formed into pellets that were crushed and sieved to provide particles in the 0.5-1.0 mm size range. A 4 mL (2.1 g) charge of Sn-BEA particles was loaded into a quartz mini-reactor (15 mm ID) equipped with a thermowell (5 mm OD) and heated to 550° C. overnight under flowing air (20 mL/min) in a 1-inch tube furnace. Air was purged from the reactor by flowing nitrogen (20 mL/min) and the catalyst bed brought to 450° C. After 10 minutes, the nitrogen flow was replaced by ammonia (50 mL/min) and after a further 10 minutes a stream of acetaldehyde ($CH_3CHO$) vapor (4.8 g/hour, ca. 1 sec contact time) was delivered directly to the front edge of the catalyst bed via a stainless-steel transfer line. The condensed reactor effluent was collected (10° C.) over a 1-hour period, weighed, and then analyzed by gas chromatography. The weight yields (grams of compound formed per gram $CH_3CHO$ fed) for α-picoline, γ-picoline, pyridine, and $CH_3CN$ were 0.388, 0.087, 0.010, and 0.055, respectively.

Example 2

The Sn-BEA catalyst from Example 1 was evaluated over several reaction-regeneration cycles. After a 4-hour reaction period, the $CH_3CHO$ flow was stopped and the $NH_3$ flow continued for 10 minutes. The $NH_3$ flow was replaced by nitrogen (10 minutes) before being replaced by air and raising the reactor temperature to 550° C. (overnight) to complete a reaction-regeneration cycle. After four reaction-regeneration cycles, the Sn-BEA catalyst was tested at a reaction temperature of 420° C. with $NH_3$ (30 mL/min) and $CH_3CHO$ (3 g/h) corresponding to a contact time of 1.7 seconds. Analysis of the recovered liquid reaction crude from the initial hour on stream gave weight yields for α-picoline, γ-picoline, pyridine, and $CH_3CN$ of 0.430, 0.108, 0.008, and 0.063, respectively.

Example 3: Synthesis of Dealuminated Zeolite Beta (deAlBEA)

A nitric acid dealumination procedure similar to that reported by Sels et al. (*Green Chemistry* 2013, 15, 2777-2785) was used. In a 3-liter round-bottomed flask fitted with an overhead stirrer, 500 mL of 13 M nitric acid was heated to 80° C. before adding 50 g of $NH_4$-BEA(25) (Zeolyst, CP814E, $SiO_2/A_2O_3 \approx 25$ or Si:Al 12.5:1) powder. The resulting slurry was maintained at 80° C. overnight and then transferred onto a Buchner filter funnel. The resulting filter cake was washed with deionized water (>3 liters) until the filtrate reached a pH of 5. The cake was dried overnight in a fan oven at 60° C. Prior to conversion into a tin-grafted catalyst, the deAlBEA was activated at 150° C. overnight.

Example 4: Synthesis of Sn-deAlBEA Via $SnCl_4$-Grafted on deAlBEA

A catalyst designated Sn-deAlBEA was synthesized using a similar dealumination-grafting procedure as reported by Sels et al. (*Green Chemistry* 2013, 15, 2777-2785). A solution was prepared under a nitrogen atmosphere by dissolving 100 g of $SnCl_4.5H_2O$ in 1 liter of isopropanol (iPrOH, 99.7%, Sigma Aldrich). Freshly activated deAlBEA (40 g) was added to the stirred iPrOH solution and then brought to reflux. After 8 hours at reflux, the slurry was transferred onto a Buchner filter funnel. The resulting Sn-deAlBEA filter cake was washed with iPrOH (ca. 500 mL) and kept under suction at room temperature overnight. The Sn-deAlBEA was dried overnight in a fan oven at 80° C. and then calcined at 550° C. for 6 hours.

Figure 1:
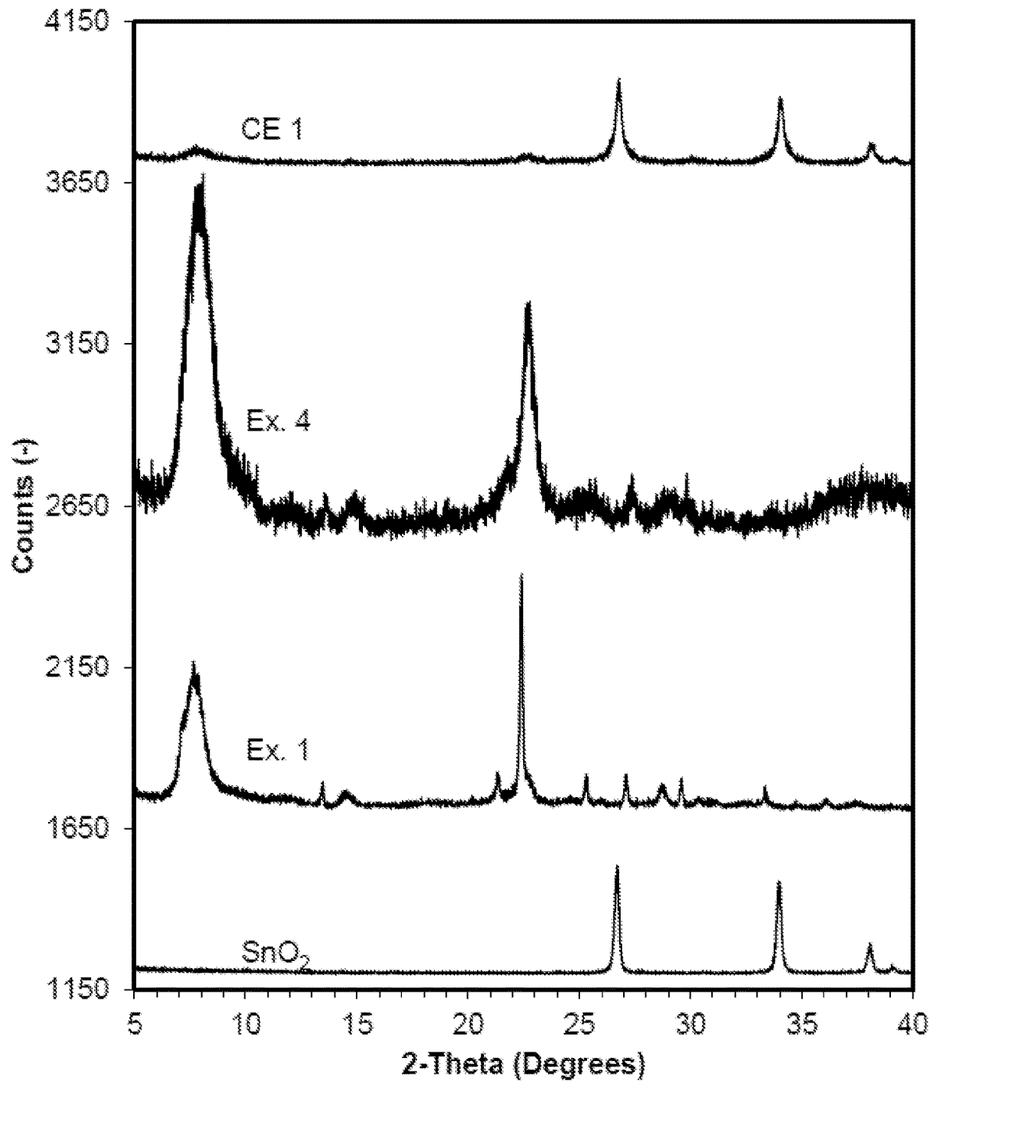
FIG. 1 shows X-ray diffraction spectra of stannic oxide, HTS Sn-BEA (Ex. 1), Sn-deAlBEA (Ex. 4), and Sn-deAlBEA (CE 1) prepared via stannous acetate at high concentration

The AAS analysis of this Sn-deAlBEA catalyst showed that it contained 1.70 wt. % tin (equivalent to 2.16 wt. % $SnO_2$) and the molar Si:Al ratio was ca. 440:1. The XRD of the Sn-deAlBEA revealed an intact BEA structure while there was no bulk $SnO_2$ (Cassiterite) evident (FIG. 1). The Sn-deAlBEA powder was formed into catalyst particles (0.5-1.0 mm size range), loaded, and tested in a minireactor using the procedure described in Example 1. At a reaction temperature of 450° C., 3 g/h of $CH_3CHO$, and 30 mL/minute $NH_3$ (1.6 s contact time), the weight yield of α-picoline, γ-picoline, pyridine, and $CH_3CN$ were 0.410, 0.116, 0.018, and 0.014, respectively.

Example 5: Synthesis of Sn-deAlBEA Via $SnCl_4$-Grafted on deAlBEA

Dealuminated zeolite Beta was prepared using a similar dealumination process described in Example 3 except that 2 liters of $HNO_3$ and 140 g of $NH_4$—BEA(25) (Zeolyst, CP814E) powder were used. The resulting deAlBEA had a molar Si:Al ratio ca. 366:1 as measured by AAS. The tin grafting process described in Example 4 was repeated except that 20 g of the heat-activated deAlBEA was added to 50 g of $SnCl_4.5H_2O$ in 1 liter of iPrOH. The resulting Sn-deAlBEA catalyst contained 1.46 wt. % Sn as measured by AAS. The XRD revealed an intact BEA structure while no $SnO_2$ phase was evident.

The Sn-deAlBEA catalyst was evaluated over several reaction-regeneration cycles using a similar procedure to that described in Example 2. Table 1 provides product weight yields from the initial hour on stream over several reaction cycles with different reaction temperatures using feed flow rates of 3 g/h $CH_3CHO$ and 30 mL/minute $NH_3$.

Following an initial break-in period, a reaction temperature in the 420-450° C. range appears to give the best α-picoline yield.

TABLE 1

| Reaction cycle | Bed temp (° C.) | α-picoline (g/g $CH_3CHO$) | γ-picoline (g/g $CH_3CHO$) | pyridine (g/g $CH_3CHO$) | $CH_3CN$ (g/g $CH_3CHO$) |
|---|---|---|---|---|---|
| 1 | 450 | 0.338 | 0.094 | 0.020 | 0.038 |
| 2 | 450 | 0.381 | 0.099 | 0.014 | 0.030 |
| 3 | 450 | 0.387 | 0.099 | 0.013 | 0.019 |
| 4 | 450 | 0.369 | 0.098 | 0.013 | 0.078 |
| 5 | 420 | 0.400 | 0.103 | 0.009 | 0.035 |
| 6 | 390 | 0.337 | 0.053 | 0.005 | 0.011 |

Example 6: Synthesis of Sn-deAlBEA Via $SnCl_4$-Grafted on deAlBEA

Dealuminated zeolite Beta was prepared using a similar dealumination process described in Example 3 except that 2 liters of $HNO_3$ and 150 g of $NH_4$—BEA(38) (Zeolyst, CP814C, $SiO_2 \sim 38$ or Si:Al ca. 19:1) powder were used. The tin grafting process described in Example 4 was repeated except that 20 g of the heat-activated deAlBEA was added to 56 g of $SnCl_4 \cdot 5H_2O$ in 1 liter of iPrOH. The Sn-deAlBEA powder was formed into catalyst particles (0.5-1.0 mm size range), loaded, and tested in a minireactor using the procedure described in Example 1. On the third reaction cycle at a reaction temperature of 420° C., 3 g/h of $CH_3CHO$, and 30 mL/minute $NH_3$, the weight yield of α-picoline, γ-picoline, pyridine, and $CH_3CN$ were 0.363, 0.109, 0.021, and 0.021, respectively.

Example 7: Synthesis of Sn-deAlBEA Via Incipient Wetness Impregnation with Aqueous $SnSO_4$ Dealuminated zeolite Beta was prepared using a similar dealumination process described in Example 3 except that 2 liters of $HNO_3$ and 200 g of $NH_4$—BEA(25) (Zeolyst, CP814E) powder were used. The resulting deAlBEA had a molar Si:Al ratio ca. 140:1 as measured by AAS. An incipient wetness impregnation (IWI) procedure was used to prepare a Sn-deAlBEA catalyst by dissolving 0.144 g of stannous sulfate ($SnSO_4$, ≥95%, Sigma Aldrich) in 17 mL of deionized water and then mixing this solution with 10 g of the heat-activated deAlBEA. The resulting paste was dried (fan oven, 80° C. overnight) and calcined (550° C., 6 h) to provide a Sn-deAlBEA catalyst with a nominal $SnO_2$ content of 1 wt. %. Catalyst particles in the 0.5-1.0 mm size range were prepared using the forming process described in Example 1.

The Sn-deAlBEA catalyst was evaluated over several reaction-regeneration cycles using a similar procedure to that described in Example 2. Table 2 provides product weight yields from the initial hour on stream over several reaction cycles with different reaction temperatures using feed flow rates of 3 g/h $CH_3CHO$ and 30 mL/minute $NH_3$.

TABLE 2

| Reaction cycle | Bed temp (° C.) | α-picoline (g/g $CH_3CHO$) | γ-picoline (g/g $CH_3CHO$) | pyridine (g/g $CH_3CHO$) | $CH_3CN$ (g/g $CH_3CHO$) |
|---|---|---|---|---|---|
| 1 | 450 | 0.374 | 0.142 | 0.024 | 0.023 |
| 2 | 450 | 0.372 | 0.133 | 0.021 | 0.036 |

TABLE 2-continued

| Reaction cycle | Bed temp (° C.) | α-picoline (g/g CH$_3$CHO) | γ-picoline (g/g CH$_3$CHO) | pyridine (g/g CH$_3$CHO) | CH$_3$CN (g/g CH$_3$CHO) |
|---|---|---|---|---|---|
| 3 | 450 | 0.384 | 0.140 | 0.017 | 0.063 |
| 4 | 420 | 0.384 | 0.146 | 0.013 | 0.025 |

Example 8: Synthesis of Sn-deAlBEA Via Aqueous SnCl$_4$ IWI with Nominally 1 wt. % SnO$_2$ An IWI procedure similar to Example 7 was used to prepare a Sn-deAlBEA catalyst with nominally 1 wt. % SnO$_2$ except that SnCl$_4$.5H$_2$O (0.235 g in 30 mL deionized H$_2$O) was used with 10 g of a deAlBEA support having a molar Si:Al ratio of ca. 150:1. Table 3 provides product weight yields from the initial hour on stream over several reaction cycles with different reaction temperatures using feed flow rates of 3 g/h CH$_3$CHO and 30 mL/minute NH$_3$.

TABLE 3

| Reaction cycle | Bed temp (° C.) | α-picoline (g/g CH$_3$CHO) | γ-picoline (g/g CH$_3$CHO) | pyridine (g/g CH$_3$CHO) | CH$_3$CN (g/g CH$_3$CHO) |
|---|---|---|---|---|---|
| 1 | 450 | 0.358 | 0.136 | 0.034 | 0.012 |
| 2 | 450 | 0.400 | 0.133 | 0.025 | 0.022 |
| 3 | 420 | 0.414 | 0.138 | 0.019 | 0.015 |

Example 9: Synthesis of Sn-deAlBEA Via Sn(CH$_3$CO$_2$)$_2$-Grafted on deAlBEA Dealuminated zeolite Beta was prepared using a similar dealumination process described in Example 3 except that 2 liters of HNO$_3$ and 200 g of NH$_4$—BEA(25) (Zeolyst, CP814E) powder were used. The resulting deAlBEA had a molar Si:Al ratio ca. 67:1 as measured by AAS. The tin grafting process described in Example 4 was repeated except that 10 g of the heat-activated deAlBEA was added to a solution containing 1.89 g of stannous acetate (Sn(CH$_3$CO$_2$)$_2$) in 1 liter of iPrOH. The resulting Sn-deAlBEA catalyst contained 4.7 wt. % Sn as measured by AAS. The XRD revealed an intact BEA structure while no SnO$_2$ phase was evident. Table 4 provides peak α-picoline weight yields when testing this Sn-deAlBEA catalyst between 390 and 450° C. using feed flow rates of 3 g/h CH$_3$CHO and 30 mL/minute NH$_3$.

TABLE 4

| Ex. | Sn wt % AAS | Calc. SnO$_2$ wt % | Bed temp (° C.) | α-picoline (g/g CH$_3$CHO) | γ-picoline (g/g CH$_3$CHO) | pyridine (g/g CH$_3$CHO) | CH$_3$CN (g/g CH$_3$CHO) |
|---|---|---|---|---|---|---|---|
| 9a | 4.7 | 6.0 | 450 | 0.200 | 0.092 | 0.013 | 0.300 |
| 9b | 4.7 | 6.0 | 420 | 0.350 | 0.162 | 0.011 | 0.034 |
| 9c | 4.7 | 6.0 | 390 | 0.348 | 0.158 | 0.012 | 0.023 |
| CE1a | 23.7 | 30.0 | 450 | 0.132 | 0.065 | 0.005 | 0.371 |
| CE1b | 23.7 | 30.0 | 420 | 0.196 | 0.089 | 0.002 | 0.202 |

Examples 10-15: Sn-deAlBEA Via Aqueous SnCl$_4$ IWI with Nominally 0.5 to 5 wt. % SnO$_2$ The IWI procedure in Example 8 was used to prepare six Sn-deAlBEA catalysts with nominal wt. % SnO$_2$ contents of 0.5%, 1.5%, 2%, 3%, 4%, and 5% using the same deAlBEA powder (Si:Al ca. 150:1). Table 5 provides peak α-picoline weight yields when testing these Sn-deAlBEA catalysts between 390 and 450° C. using feed flow rates of 3 g/h CH$_3$CHO and 30 mL/minute NH$_3$.

TABLE 5

| Ex. | Nom. SnO$_2$ wt % | Bed temp (° C.) | α-picoline (g/g CH$_3$CHO) | γ-picoline (g/g CH$_3$CHO) | pyridine (g/g CH$_3$CHO) | CH$_3$CN (g/g CH$_3$CHO) |
|---|---|---|---|---|---|---|
| 10 | 0.5 | 450 | 0.389 | 0.129 | 0.0025 | 0.008 |
| 11 | 1.5 | 450 | 0.399 | 0.125 | 0.022 | 0.017 |
| 12 | 2.0 | 450 | 0.416 | 0.132 | 0.019 | 0.025 |
| 13 | 3.0 | 450 | 0.395 | 0.129 | 0.019 | 0.024 |
| 14 | 4.0 | 420 | 0.400 | 0.148 | 0.011 | 0.057 |
| 15 | 5.0 | 390 | 0.382 | 0.130 | 0.008 | 0.014 |

Example 16: Formation of α-Parvoline (2-Ethyl-3,5-Dimethylpyridine) from Propanal (CH$_3$CH$_2$CHO) and NH$_3$ Following overnight air regeneration at 550° C., the Sn-deAlBEA catalyst from Example 4 was tested with a CH$_3$CH$_2$CHO—NH$_3$ feed mixture at 380° C. and feed flow rates of 2.7 g/h CH$_3$CH$_2$CHO and 36 mL/minute NH$_3$. The weight yield of α-parvoline and γ-parvoline (4-ethyl-3,5-dimethylpyridine) was 0.667 and, 0.013, respectively.

Example 17: 1% SnO$_2$ 0.25% ZnO

Using a similar IWI procedure and deAlBEA support as described in Example 8, a Sn—Zn-deAlBEA catalyst was prepared using an aqueous solution containing SnCl$_4$.5H$_2$O and zinc nitrate (Sigma-Aldrich) to provide nominal SnO$_2$ and ZnO loadings of 1.0 and 0.25 wt. %, respectively. At a reaction temperature of 450° C., 3 g/h of CH$_3$CHO, and 30 mL/minute NH$_3$, the weight yield of α-picoline, γ-picoline, pyridine, and CH3CN were, 0.416, 0.143, 0.017, and 0.012, respectively.

Example 18: Synthesis of Ti-deAlBEA Via Ti(OiPr)$_4$-Grafted on deAlBEA

A 20 g amount of heat-activated deAlBEA, prepared as described in Example 5, was added to a stirred solution containing 49 g of titanium(IV) isopropoxide (Sigma Aldrich) in 1 L of iPrOH under a nitrogen atmosphere. The resulting slurry was brought to reflux and after 8 hours filtered and washed with 500 mL of iPrOH. The resulting Ti-deAlBEA filter cake was dried (80° C.), calcined (550° C., 6 h.), pressed, and formed into 0.5-1.0 mm size range catalyst particles. Table 6 shows the results of testing this catalyst at 450° C. with flow rates of 3 g/h CH$_3$CHO and 30 mL/minute NH$_3$. The Ti-deAlBEA catalyst gave a good combined weight yield of α-picoline and pyridine, the latter compound being of greater value than γ-picoline.

Examples 19-22: Synthesis of Mn-, Fe-, Co-, and Zn-deAlBEA Via Aqueous IWI of Nitrate Salts An aqueous IWI procedure similar to that described in Example 7 was used to prepare Mn-, Fe-, Co-, and Zn-deAlBEA catalysts using a dealuminated zeolite Beta with a Si/Al molar ratio of ca. 150. Each catalyst had a nominal metal oxide content of 0.45 wt. % starting from aqueous solutions of Mn(II), Fe(III), Co(II), and Zn(II) nitrate salts (all supplied by Sigma Aldrich). The formed catalysts were evaluated over a range of temperatures (3 g/h CH$_3$CHO, 30 mL/minute NH$_3$, 550° C. air regeneration between runs) and Table 6 reports conditions that gave the maximum α-picoline weight yield. All of the metal promoters gave good α-picoline weight yields while the less active Fe- and Mn-based catalysts gave significant incremental pyridine.

TABLE 6

| Ex. | Cat. | MO$_x$ | Nom. M$_y$O$_x$ wt % | Bed temp (° C.) | α-picoline (g/g CH$_3$CHO) | γ-picoline (g/g CH$_3$CHO) | pyridine (g/g CH$_3$CHO) | CH$_3$CN (g/g CH$_3$CHO) |
|---|---|---|---|---|---|---|---|---|
| 18 | Ti-deAlBEA | TiO$_2$ | nd | 450 | 0.300 | 0.109 | 0.057 | 0.025 |
| 19 | Mn-deAlBEA | MnO$_2$ | 0.45 | 510 | 0.331 | 0.111 | 0.049 | 0.064 |
| 20 | Fe-deAlBEA | Fe$_2$O$_3$ | 0.45 | 480 | 0.333 | 0.117 | 0.050 | 0.034 |
| 21 | Co-deAlBEA | Co$_3$O$_4$ | 0.45 | 420 | 0.303 | 0.131 | 0.021 | 0.035 |
| 22 | Zn-deAlBEA | ZnO | 0.45 | 450 | 0.334 | 0.144 | 0.023 | 0.054 |

Example 23: Synthesis of CIT-6 and Zn-CIT-6

Beta zeolite with framework Zn atoms (CIT-6) was prepared using the procedure reported by Davis et al., (*J. Phys. Chem. B.* 1999, 103, 2674-2679). CIT-6 was prepared by adding 0.99 g of zinc acetate dihydrate (Sigma Aldrich, 99.9%) and 0.316 g of lithium hydroxide monohydrate (Sigma Aldrich, 99.95%) to 46.73 g of water and 22.87 g of tetraethylammonium hydroxide (Sigma Aldrich, 40 wt. %). The mixture was stirred for about 15 minutes until all the solids were completely dissolved. The mixture was then added with 22.87 g of colloidal silica (Sigma Aldrich, 40 wt. %) and stirred for 2 hours. The final reaction mixture gel had the following molar composition: 0.65 TEA$^+$: 1.0 SiO$_2$: 0.05 Li$^+$: 0.03 Zn(CH$_3$COO)$_2$: 0.70 OH$^-$: 30 H$_2$O. The gel was then charged to Teflon-lined, stainless steel autoclaves (Parr Instrument Co.) and was heated statically at 140° C. for 138 hours in a forced convection oven. The product was collected by centrifugation and washed with purified water and acetone (5 times each, ca. 50 mL/g of zeolite per wash) and then oven dried overnight at 90° C.

The as-made CIT-6 was ion exchanged from the lithium form to the zinc form using an adaptation of the procedure reported by Andy and Davis (*Ind. Eng. Chem. Res.* 2004, 43, 2922-2928). A zinc nitrate solution (1 M, ca. 480 mL) was added to 4.8 g of as-made CIT-6 and stirred at 500 RPM and 80° C. for 10 hours. The resulting solids were washed with water and acetone 5 times each (ca. 50 mL/g zeolite per wash) and dried in a vacuum furnace (ca. 0.013 kPa) overnight at ambient temperature. The dry Zn-CIT-6 powder was then heated (muffle furnace, 1° C./minute) under flowing air to 580° C. and held for 10 hours.

The resulting Zn-CIT-6 powder was formed into catalyst pellets and evaluated for the formation of α-picoline over a range of temperatures (3 g/h CH$_3$CHO, 30 mL/minute NH$_3$, 550° C. air regeneration between runs). The maximum α-picoline weight yield was obtained at 360° C. were the weight yields for α-picoline, γ-picoline, pyridine, and CH$_3$CN were 0.293, 0.125, 0.010, and 0.026, respectively.

Comparison Example 1: Synthesis of Sn-deAlBEA Via Sn(CH$_3$CO$_2$)$_2$-Grafted on deAlBEA The tin grafting procedure in Example 9 was modified by using a ten-fold higher concentration of Sn(CH$_3$CO$_2$)$_2$ (19 g in 1 L iPrOH) together with the batch of deAlBEA (10 g) described in Example 5. The resulting Sn-deAlBEA catalyst contained 23.7 wt. % Sn as measured by AAS. The XRD (FIG. 1) revealed an intact BEA structure together with the presence of a significant amount of SnO$_2$ phase (Cassiterite). Table 4 provides peak α-picoline weight yields when testing this Sn-deAlBEA catalyst between 420 and 450° C. using feed flow rates of 3 g/h CH$_3$CHO and 30 mL/minute NH$_3$.

Formation of bulk crystalline SnO$_2$ in the higher tin content Sn-deAlBEA catalyst is detrimental to performance leading to excessive acetonitrile formation compared to α-picoline.

What is claimed is:

1. A process for preparing a pyridine base comprising contacting ammonia with a C$_2$-C$_6$ aldehyde in the presence of a metal loaded zeolite beta catalyst comprising a metal and a zeolite beta,
   wherein the metal loaded zeolite beta catalyst is prepared by a process comprising
   i. contacting tetraethyl orthosilicate with aqueous tertaethylammonium hydroxide to provide a silicate solution;
   ii. contacting the silicate solution with a metal source to provide a metal-silicate solution;
   iii. contacting the metal-silicate solution with hydrofluoric acid to provide a metal-silicate gel; and
   iv. contacting the metal-silicate gel with dealuminated zeolite beta seeds to provide the metal loaded zeolite beta catalyst.

2. The process of claim 1, wherein the metal source is a Sn containing compound.

3. The process of claim 1, wherein the metal source is aqueous stannic chloride.

4. The process of claim 3, wherein the metal loaded zeolite beta catalyst has a zeolite beta topology and an absence of bulk crystalline SnO$_2$.

5. The process of claim 4, wherein the tin content of the metal loaded zeolite beta catalyst is from about 1 wt % to about 4 wt %.

6. The process of claim 1, wherein the metal loaded zeolite beta catalyst comprises a metal and a dealuminated zeolite beta.

7. The process of claim 6, wherein the dealuminated zeolite beta has a SiO$_2$/Al$_2$O$_3$ molar ratio of at least about 150/1.

8. The process of claim 7, wherein the metal is in an amount of less than about 10% by weight compared to the metal loaded zeolite beta catalyst.

9. The process of claim 8, wherein the metal selected from the group consisting of Sn, Ti, Mn, Fe, Co, Zn, and combinations thereof.

10. A process for preparing a pyridine base comprising contacting ammonia with a C$_2$-C$_6$ aldehyde in the presence of a metal loaded zeolite beta catalyst comprising a metal and a zeolite beta, wherein the metal loaded zeolite beta catalyst is prepared by a process comprising
contacting a dealuminated zeolite beta with a metal source to provide the metal loaded zeolite beta catalyst.

11. The process of claim 10, wherein the dealuminated zeolite beta is provided by
contacting a zeolite beta catalyst having a $SiO_2/Al_2O_3$ molar ratio of about 15 to about 90 with a mineral acid.

12. The process of claim 11, wherein the mineral acid is selected from the group consisting of nitric acid, hydrochloric acid and phosphoric acid.

13. The process of claim 1, wherein the metal loaded zeolite beta catalyst is mixed and formed with a binder selected from the group consisting of $SiO_2$, $Al_2O_3$, kaolin, montmorillonite, and titania to provide a metal loaded zeolite beta catalyst composition.

14. The process of claim 1, wherein the $C_2$-$C_6$ aldehyde is selected from the group consisting of acetaldehyde, propionaldehyde, crotonaldehyde and butyraldehyde.

15. The process of claim 1, further comprising
regenerating the metal loaded zeolite beta catalyst remaining after step of contacting ammonia with a $C_2$-$C_6$ aldehyde by contacting the metal loaded zeolite beta catalyst with air at a temperature of from about 500° C. to about 600° C.

16. The process of claim 15, further comprising contacting ammonia with a $C_2$-$C_6$ aldehyde in the presence of the metal loaded zeolite beta catalyst obtained from the step of regenerating the metal loaded zeolite beta catalyst.

17. The process of claim 1, wherein the pyridine base is α-picoline.

18. The process of claim 1 wherein the pyridine base is α-picoline and the α-picoline is formed in a ratio of at least about 2.5:1 of a-picoline to y-picoline side-product.

19. The process of claim 1, wherein the pyridine base is α-parvoline.

20. The process of claim 10, wherein the metal source is $SnO_2$, $SnCl_2$, $SnSO_4$, or $Sn(CH_3CO_2)_2$.

* * * * *